(12) United States Patent
Fischer et al.

(10) Patent No.: US 10,344,055 B2
(45) Date of Patent: Jul. 9, 2019

(54) COMPOSITION COMPRISING A PEPTIDE AND AN INHIBITOR OF VIRAL NEURAMINIDASE

(75) Inventors: Bernhard Fischer, Vienna (AT); Rudolf Lucas, Aartselaar (BE); Hendrik Fischer, Vienna (AT)

(73) Assignee: Apeptico Forschung UND Entwicklung GMBH, Vienna (AT)

( * ) Notice: Subject to any disclaimer, the term of this patent is extended or adjusted under 35 U.S.C. 154(b) by 0 days.

(21) Appl. No.: 13/885,705

(22) PCT Filed: Nov. 15, 2011

(86) PCT No.: PCT/AT2011/000462
§ 371 (c)(1),
(2), (4) Date: Jun. 20, 2013

(87) PCT Pub. No.: WO2012/065201
PCT Pub. Date: May 24, 2012

(65) Prior Publication Data
US 2013/0261048 A1    Oct. 3, 2013

(30) Foreign Application Priority Data

Nov. 18, 2010    (AT) .................. A 1908/2010

(51) Int. Cl.
*C07K 7/64* (2006.01)
*A61K 38/19* (2006.01)
*A61K 45/06* (2006.01)

(52) U.S. Cl.
CPC .............. *C07K 7/64* (2013.01); *A61K 38/191* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,069,819 A | 1/1978 | Maiorano | |
| 4,995,385 A | 2/1991 | Ceschel et al. | |
| 5,186,166 A * | 2/1993 | Riggs ................... | A61M 15/00 128/203.15 |
| 5,360,817 A | 11/1994 | Danylec et al. | |
| 5,453,533 A | 9/1995 | Luo et al. | |
| 5,512,596 A | 4/1996 | Kim et al. | |
| 5,602,277 A | 2/1997 | Babu et al. | |
| 5,763,483 A | 6/1998 | Bischofberger et al. | |
| 5,866,601 A | 2/1999 | Kim et al. | |
| 5,886,213 A | 3/1999 | Kelly et al. | |
| 5,952,375 A | 9/1999 | Bischofberger et al. | |
| 5,958,973 A | 9/1999 | Bischofberger et al. | |
| 6,340,702 B1 | 1/2002 | Honda et al. | |
| 6,410,594 B1 | 6/2002 | Babu et al. | |
| 6,451,766 B1 | 9/2002 | Honda et al. | |
| 6,455,571 B1 | 9/2002 | Maring et al. | |
| 6,509,359 B1 | 1/2003 | Brouillette et al. | |
| 6,518,305 B1 | 2/2003 | Maring et al. | |
| 6,593,314 B1 | 7/2003 | Maring et al. | |
| 6,831,096 B2 | 12/2004 | Maring et al. | |
| 2007/0299003 A1 | 12/2007 | Schaefer et al. | |
| 2008/0063722 A1 | 3/2008 | Ward et al. | |
| 2008/0227743 A1* | 9/2008 | Nguyen et al. .................. | 514/44 |

FOREIGN PATENT DOCUMENTS

| | | |
|---|---|---|
| AT | 506150 A1 | 6/2009 |
| EP | 1781323 A1 | 5/2007 |
| EP | 1264599 B1 | 9/2007 |
| JP | 2008-509107 | 4/2006 |
| JP | 2010-138081 | 6/2010 |
| RU | 2181357 C2 | 4/2002 |
| WO | 02/09699 A2 | 3/2002 |
| WO | 02/09699 A2 | 7/2002 |
| WO | 2008/099874 A1 | 8/2008 |
| WO | 2010/099566 A1 | 9/2010 |
| WO | 2010099556 A1 | 9/2010 |
| WO | WO 2010/099556 * | 9/2010 |

OTHER PUBLICATIONS

The WHO (http://www.who.int/mediacentre/factsheets/fs211/en/ accessed Mar. 28, 2014).*
CDC (http://www.cdc.gov/flu/about/disease/symptoms.htm) (accessed Mar. 31, 2014).*
Rollinger et al. (Current development in natural products chemistry, vol. 29 (11) 2012, Influenza neuraminidase: a druggable target for natural products).*
Poland et al. (A Plea for Rational Use; Clinical Infectious Diseases; 2009; 48:1254-6).*
Smee et al. ("Combinations of oseltamivir and peramivir for the treatment of influenza A (H1N1) virus infections in cell culture and in mice" Antiviral Research. Oct. 2010; 88(1):38-44).*
Austrian Office Action 4A A 1908/2010-1 dated Apr. 19, 2011.
International Search Report and Written Opinion PCT/AT2011/000462 dated "Unknown".
International Preliminary Report on Patentability PCT/AT2011/00462 dated Jan. 17, 2013.
Elia, Nadia, et al., "Functional Identification of the Alveolar Edema Reabsorption Activity of Murine Tumor Necrosis Factor-a," 2003 Am J Respir Crit Care Med vol. 168 pp. 1043-1050.
Hribar, Marusa, et al., "The lectin-like domain of tumor necrosis factor-a increases membrane conductance in microvascular endothelial cells and peritoneal macrophages," 1999 Eur. J. Immunol. vol. 29 pp. 3105-3111.

(Continued)

*Primary Examiner* — James H Alstrum-Acevedo
*Assistant Examiner* — Tara L Martinez
(74) *Attorney, Agent, or Firm* — Chainey P. Singleton

(57) ABSTRACT

Described is a composition comprising—a peptide which consists of 7-17 adjacent amino acids and comprises the hexamer $TX_1EX_2X_3E$, where $X_1$, $X_2$ and $X_3$ can be any natural or non-natural amino acid, and the peptide is cyclized and does not exhibit TNF receptor binding activity, and—an inhibitor of viral neuraminidase.

Figure 1:
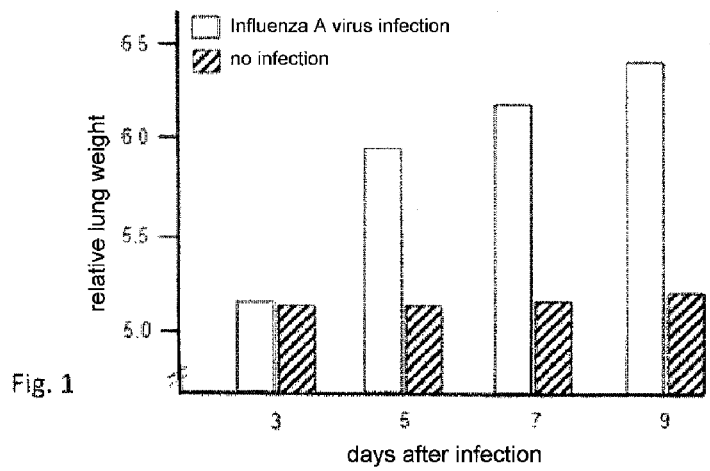
Figure 2:
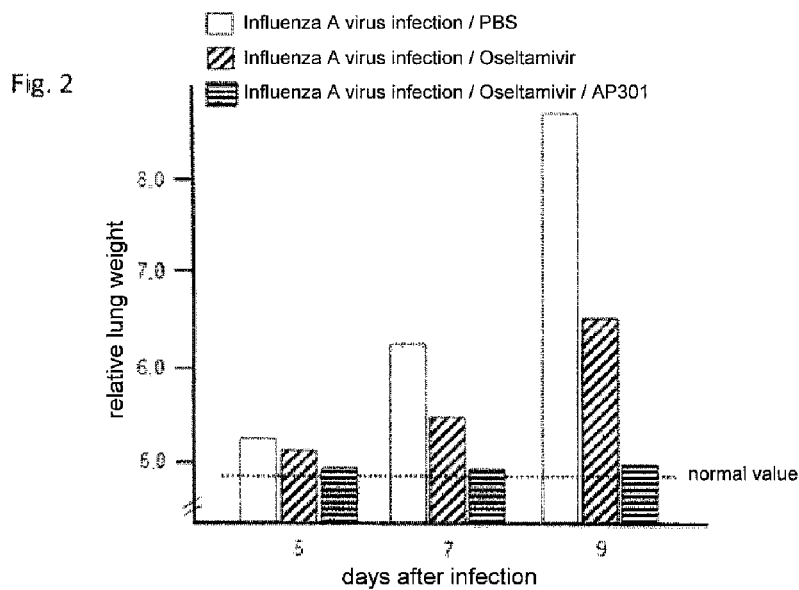

15 Claims, 2 Drawing Sheets
Specification includes a Sequence Listing.

(56) References Cited

OTHER PUBLICATIONS

Yang Lingzhi et al., "Expression and Application of Neuraminidase of Influenza Virus", China Biotechnology, vol. 29 No. 5, pp. 6-10, 2009.
Office Action, State Intellectual Property Office, P.R. China, CN201180055463.2 dated Nov. 15, 2014.
JP Office Action; JP 2013-539088 dated Oct. 6, 2015 (Translation).
Anne Moscona, M.D.; "Neuraminidase Inhibitors for Influenza"; The New England Journal of Medicine 353;13; Sep. 29, 2005; pp. 1363-1373.
Korean Office Action (English Version); Dec. 13, 2017; pp. 1-5.
Korean Office Action (Korean Version); Dec. 13, 2017; pp. 1-8.
RU 2013 127 402 [Russian Patent Office] Office Action dated Nov. 19, 2015 (English Trans included).
CN 201180055463.2 Reexamination Decision dated Nov. 15, 2016.
Identification and Management of Critical Emergencies, Lai Rongde and Li Qilin, Science and Technology Literature Publishing House, p. 689 "I. The treatment of anti-avian influenza viruses" published in Apr. 2009. (English Translation).

\* cited by examiner

COMPOSITION COMPRISING A PEPTIDE AND AN INHIBITOR OF VIRAL NEURAMINIDASE

CROSS REFERENCE TO RELATED APPLICATION

This application is the National Stage of International Application No. PCT/AT2011/000462, filed on 15 Nov. 2011 claiming the priority of A 1908/2010, filed on 18 Nov. 2010, the content of each of which is incorporated by reference herein.

The present invention relates to pharmaceutical compositions for the treatment of influenza.

In humans, influenza is a serious disease of the respiratory tract and of the whole organism, which is caused by influenza viruses. The influenza viruses belong to the family of orthomyxoviruses, which are characterized by a segmented RNA genome in a negative strand orientation. The types relevant to humans are the influenza A and B viruses, of which subtype A in particular is known as a causative agent of highly feverish diseases of the respiratory tract. Besides the veterinary importance, all influenza viruses have a zoonitic potential, i.e. there is a possibility of transmission from a chicken or pig to a human being.

Influenza emerges periodically as a pandemic which in most cases has its origine in South East Asia and China and spreads worldwide from there. Pandemics of influenza viruses are associated with a high number of deaths not only with elderly persons but also with juveniles. According to the WHO, the annual seasonal influenza results in a worldwide rate of 3 to 5 million cases of a severe disease, with a death rate of 250,000 to 500,000. The most frequent cause of death is an influenza pneumonia with resulting lung failure, but cardiovascular damages such as myocarditis (myocardial inflammation) or pericarditis (inflammation of the pericardial sac) may occur as well. Further rather frequent causes of death can be an inflammation of the brain or the meninges (meningoencephalitis) or the damage of other organ systems (in particular the kidneys).

Normally, the incubation period is 4 to 5 days, but it may be shorter. The disease starts out with a sudden onset of headaches, shivering, chills and cough. This is followed by a high fever of up to 41° C., muscles pains, loss of appetite and a general sense of weakness. This phase lasts for about 3 days, following which the fever declines and is in most cases sunk back to normal values from the sixth day on, which means the virus is eliminated out of the body. The cough may last for several weeks.

A severe, life-threatening influenza may occur if a primary viral interstitial (in many cases hemorrhagic) pulmonary inflammation is developing following the above described symptoms. In addition to weakened persons, it also occurs in approximately 25% of healthy or not predamaged persons and may last up to 2 weeks. Such a pulmonary inflammation may be detected by measuring an increase in the lung weight.

Pneumonias may also develop secundarily by bacterial superinfections (among others by *Streptococcus pneumoniae*, *Staphylococcus aureus* and *Hemophilus influenzae*). Further factors contributing to these complications are, among others, other pulmonary diseases (e.g. asthma), immunodeficiency, age (infants and elderly persons), diabetes, lung injuries, smoking. Therefore, persons having these complications are the primary target group for a vaccination.

Influenza viruses reach into the organism by droplet infection and infect by binding the HA protein to terminal neuraminic acid residues on the epithelial cells of the oral, nasal and pharyngeal mucosa. From there, they spread to the lower respiratory tract. Destructions of cells can be observed in ciliated epithelia and in mucigenous skin layers of all areas of the respiratory tract. If a primary, interstitial pulmonary inflammation is developing, the virus is transferred to the cells of the lung parenchyme. Strong swellings of the alveolar walls can be seen, the epithelium of which often becomes entirely ablated by the cell destruction. Such a swelling of the lung tissue can be detected by measuring an increase in the lung weight.

There are both, prophylactic and therapeutic treatments, and vaccines against both, influenza A and B infections, are available. These consist of killed viruses which were grown in chicken eggs and/or cell culture. The protection provided by the vaccine has reached its full effectiveness approximately two weeks after the vaccination. However, due to the high variability of the influenza viruses, the vaccines must be adapted to the currently circulating virus subtypes or variants of subtypes annually.

In addition, inhibitors of viral neuraminidase (Zanamivir, Oseltamivir) are being applied which prevent the release of newly replicated virus particles from the host cell. They are preferably used shortly after an occurred and detected influenza virus infection in order to constrain the spread of the virus in an early infection phase (WO 2003/026567 A2).

However, the inhibitors of viral neuraminidase merely interfere with the proliferation of viruses but cannot inactivate viruses that are already present in the body. Neuraminidase inhibitors may contribute to shortening the duration of disease only minimally (on the average by one day in humans).

It is a goal of the present invention to significantly increase the therapeutic effect of such inhibitors of virus proliferation. The present invention aims at providing improved pharmaceutical compositions for the treatment of infections with influenza viruses.

Accordingly, the present invention relates to a composition comprising
- a peptide, which consists of 7-17 adjacent amino acids and comprises the hexamer $TX_1EX_2X_3E$, wherein $X_1$, $X_2$ and $X_3$ can be any natural or non-natural amino acid, and wherein the peptide has no TNF receptor binding activity and is cyclized, and
- an inhibitor of viral neuraminidase, in particular for the application of preventing and treating influenza.

It was now found according to the invention that the effect of neuraminidase inhibitors can surprisingly be improved by using a peptide, as defined above, in combination with a neuraminidase inhibitor for the treatment of influenza infections. The prophylactic use of the compound according to the invention is thereby indicated, too. The present invention has proved to be particularly efficient in the treatment of pulmonary inflammations which are induced by the influenza viruses.

The peptides to be used according to the invention are known, for example, from European Patent EP 1 264 599 B1 (or from US 2007/299003 A, WO 94/18325 A1 or WO 2008/148545 A1) and have been used in the prior art for treating fluid accumulations (pulmonary edema) and in particular for reabsorbing these fluid accumulations. Surprisingly, these peptides are also appropriate for influencing the fluid flow in the inverse direction via the endothelium of the capillaries into the epithelium of the lungs and can thus be employed to prevent and treat hyperpermeability of epithelial cells and endothelial cells as well (WO 2010/099556 A).

These peptides, which are known per se and which are used together with the neuraminidase inhibitor according to the invention, do not exhibit any TNF receptor binding activity (Hribar et al., Eur. J. Immunol. 1999; Elia et al., AJRCCM 2003; see also: Example part below) and are cyclized. Preferred variants of these peptides consist of 7-17 adjacent amino acids and contain the hexamer TPEGAE (SEQ ID NO: 4).

While WO 2010/099556 A1 and EP 1 264 599 A1 are targeted to the treatment of certain pathological symptoms in the lung and not to the prevention and treatment of a disease by a certain pathogen, the application according to the present invention, however, is a complete different one.

As has been shown in the course of the studies concerning the present invention, the peptides according to the claims (a.o. according to WO 2010/099556 A1) support the effect of the neuraminidase inhibitors in the combination preparation of the invention in a synergistical way. The application according to the present invention is thus targeted directly to an infection by influenza viruses and not to general symptoms, which may have been induced by several different pathogens (as is the case for example in WO 2010/099556 A1 or in EP 1 264 599 A1).

From the point of view of a person skilled in this art it is clear, however, that neuraminidase inhibitors can merely inhibit the proliferation of influenza viruses but not thereby reduce already existing viruses; it is, however, entirely surprising and not shown by the prior art that the combination of neuraminidase inhibitors and the peptides according to the invention yields a substantial improvement in the control of influenza. The prior art does not bestow any suggestions of this combination to a person skilled in the art, on the contrary:

In WO 2003/026567 A2 it is described that the neuraminidase inhibitors used for the treatment of influenza are also appropriate for preventing any influenza associated bacterial infections. Based on this document, a person skilled in the art can not at all perceive any reasons why to add further additives to the neuraminidase inhibitors, which can improve the antiviral efficiency or the effectiveness of an influenza treatment. In a particularly preferred embodiment of the present invention, the composition according to the invention is comprised of a cyclized peptide, consisting in a sequence of consecutive amino acids, selected from the group, consisting in

```
                              (SEQ ID NO: 5)
QRETPEGAEAKPWY (SEQ ID NO: 6)
PKDTPEGAELKPWY (SEQ ID NO: 1)
CGQRETPEGAEAKPWYC,
and (SEQ ID NO: 7)
CGPKDTPEGAELKPWYC
``` and fragments of at least 7 amino acids thereof, which fragments include the hexamer TPEGAE.

Preferably, the peptide in the composition is comprised of the amino acid sequence CGQRETPEGAEAKPWYC (SEQ ID NO: 1) and is cyclized via the C-residues. Thus, this particularly preferred peptide has the following amino acid sequence (SEQ ID NO: 1) (NH2) Cys-Gly-Gln-Arg-Glu-Thr-Pro-Glu-Gly-Ala-Glu-Ala-Lys-Pro-Trp-Tyr-Cys (COOH). This peptide is also referred to as "AP301".

Thereby, the cyclization of the peptides according to the invention can be achieved, for example, by a direct cyclization via a disulfide bridge between the two C-residues at the N- and C-terminus or by coupling the peptide via both cysteins to a carrier substance. In the peptides according to the invention, the cystein residues are preferably provided at the beginning and the end of the molecule. Other functional groups, which can achieve a cyclization of the peptide, may be employed as well; hereby, for example, an acidic group can accomplish an amide or ester ring closure with an amine or alcohol (for example, the amino acids asparaginic acid and glutaminic acid can be cyclized preferably intramolecularly with serine, threonine, tyrosine, asparagine, glutamine or lysine). The cyclization of the peptide is preferably effected by a disulfide bridge between the C-residues of the peptide (if present).

Thus, additional preferred peptides according to the invention are for example CGQKETPEGAEAKPWYC (SEQ ID NO: 8), CGQRETPEGAEARPWYC (SEQ ID NO: 9), CGQRETPEGAEAKPC (SEQ ID NO: 10), CQRETPEGAEAKPWYC (SEQ ID NO: 11) or CGQRETPEGAEAKFWYC (SEQ ID NO: 12).

However, the cyclization can also be accomplished by binding the peptide to carrier substances. As the carrier substances for a cyclization of this kind, all customary pharmaceutically applicable substances are eligible, which are able to covalently bind to the SH groups of the cysteins, for example (or to other naturally present or artificially introduced chemically reactive groups of the peptides); hereby, the customary carrier proteins such as keyhole limpet hemocyanine (KLH), tetanus toxin etc. are particularly preferred. Adjacent bifunctional residues on the carrier can also be envisaged (e.g. an acid group next to an amine or alcohol group). In this context, it is important to understand that the term "cyclization" comprises both, the intramolecular ring closure and the bonding to a carrier (from which the bound peptide projects out (by the N- and C-terminus of the peptide being bound to the carrier)); hereby, a peptide cyclized like this is showing the cyclic spatial structure and is stabilized appropriately.

Inhibitors of viral neuraminidase are known and have already proved themselves in the prevention and treatment of influenza. Such viral neuraminidase inhibitors (such as e.g. Zanamivir, Oseltamivir, Laninamivir or Peramivir) prevent the release of newly replicated virus particles from the host cell. In particular, the spread of viruses shortly after an occurred and detected infection with influenza viruses can be constrained by them in the early phase of infection.

These neuraminidase inhibitors, however, merely interfere with the proliferation of viruses but cannot inactivate viruses that are already present in the body. Thus, in many cases, it is merely the duration of the disease which can be shortened minimally (on the average by one day in adults). In front of all, however, the symptoms of influenza, in particular of a pneumonia, which in most cases lead to particular complications, cannot be combated or prevented efficiently enough as a rule.

Neuraminidase is an essential enzyme for the reproduction of the influenza virus, and it has been described as "molecular scissor" which is responsible for the release of the viruses.

Neuraminidase inhibitors are comprised of analogues of sialic acid, which represent a new class of the second generation of antiviral agents which show efficacy against influenza A and B viruses. Neuraminidase inhibitors according to the present invention can be all compounds suggested for it hitherto, as summarized for example in US 2008/0063722 A1 (as well as for preferred pharmaceutical formulations of such substances). These substances can inhibit at least one enzymatic activity of the neuraminidase protein of a virulent strain of the type A or type B influenza virion. Such substances can be used for both, the prophylaxis and treatment of influenza; however, in combination with the above defined peptides according to the invention, this effect is significantly improved.

Examples of neuraminidase inhibitors, which may be employed in the present composition, are described for example in U.S. Pat. Nos. 5,453,533, 5,763,483, 5,952,375, 5,958,973, 5,512,596, 5,886,213, 5,602,277, 6,410,594, 5,360,817, 5,866,601, 6,340,702, 6,451,766, 6,455,571, 6,593,314, 6,509,359, 6,518,305 and 6,831,096. Substances, which are already being employed with humans (or are at least undergoing clinical trial) and are therefore particularly preferred, are for example CS-8958 (R118958; US 2008/0063722 A1), Zanamivir (GG167, RELENZA®), Peramivir (RWJ-270201, BCX-1812), Oseltamivir phosphate (Ro64-0796, GS4104), Oseltamivir carboxylate (Ro64-0802, GS4071), or Oseltamivir (GS4104, TAMIFLU®). Of course, all effective chemical forms of the neuraminidase inhibitors are comprised according to the invention, that is salts, racemic, optically pure and/or salt-free forms (also in the form of enantiomers or diastereomers, for example).

Preferably, the inhibitor of viral neuraminidase is Zanamivir or Oseltamivir; these substances are preferred because they have already been employed particularly successfully in the treatment of humans.

Preferably, the composition according to the invention comprises a pharmaceutically acceptable carrier and is prepared in the form of a pharmaceutical composition which is suitable for administration to humans.

The expression “a pharmaceutical composition” refers to any composition, which is comprised of a neuraminidase inhibitor and a peptide as defined above (of course to appropriate (i.e. not negatively interfering with each other) mixtures of such substances, too), which prevents, improves or cures the conditions described herein. The expression “a pharmaceutical composition” refers in particular to a composition, which is comprised of a neuraminidase inhibitor and a peptide, such as described above, and a pharmaceutically acceptable carrier or excipient (both expressions may be used interchangeably). Suitable examples of carriers or excipients, which are known to someone of skill in the art, are water, isotonic solution, sodium phosphate, sodium acetate, sodium carbonate, citrate, glycine, glycylglycine, histidine, lysine, arginine, TRIS and sodium citrate or mixtures thereof. Of course, Ringer solution, dextrose solution or solutions of non-reducible sugars can be employed as well; accordingly, mannite, trehalose, saccharose, sorbite, fructose, maltose, lactose or dextrane, Hank solution, fixed oils, ethyl oleate, 5% dextrose in isotonic solution, substances, which improve the isotonicity and the chemical stability, buffers and stabilizing agents are also suitable as such carriers. Other suitable carriers include any such which do not induce by themselves the production of antibodies which will be harmful to the individual, the composition is to be administered to, such as proteins, polysaccharides, polylactic acids, polyglycolic acids, polymeric amino acids and amino acid copolymers. In formulating the composition according to the invention, the relevant guidelines (e.g. the (European or US) pharmacopoeia) have of course to be complied with. Thereby, the peptide to be provided in the composition according to the invention can also be cyclized to these carriers by direct covalent binding.

The pharmaceutical composition according to the invention can be administered (as a drug) by any appropriate method known to a person skilled in the art, and in particular it is preferable to administer the peptide to be used according to the invention or the composition according to the invention into the lung. Although influenza does play a certain role with animals, too, and the composition according to the invention can of course be employed in the prevention and prophylaxis of animals as well, the focus of the present invention is on preventing and treating humans, i.e. of persons who have already become infected with influenza or who are at risk of getting infected with this virus (especially at influenza epidemics or pandemics). The preferred administration route is inhalation (via aerosols), followed by an intravenous administration, instillation, oral administration or a combination thereof. In the inhalatory, parenteral or oral administration, the drug of this invention is formulated in unit dosage form as a solution, suspension or emulsion, which is combined with the above defined pharmaceutically acceptable excipients. In indivival cases, the dosage and administration form can of course depend on the respective individual.

Therefore, the effective amount required in each case is administered to the individual that needs the administration. The “effective amount” is to be understood as an amount effective enough to provide the intended therapeutic or prophylactic effect, for example to prevent a further spread of the disease or to effectively treat it. In most cases, an average patient is taken as a basis for this; however, the actual effective amounts of the components in the composition can be formulated in a way that is taking the administration form and the age, weight, condition of the patient as well as the degree and progress of the disease into consideration (e.g. by way of an adequate, conventional pharmacological protocol).

Preferably, the pharmaceutically acceptable carrier in the composition according to the invention is selected from water (particularly preferred: water for injection), sodium chloride, sodium phosphate, sodium acetate, sodium carbonate, citrate, glycine, glycylglycine, histidine, lysine, arginine, TRIS, sodium citrate, Ringer solution, dextrose, mannite, trehalose, saccharose, sorbite, fructose, maltose, lactose or dextrane, Hank solution, fixed oils, ethyl oleate, substances, which improve the isotonicity and the chemical stability, stabilizing agents, pharmaceutically acceptable proteins, polysaccharides, polylactic acids, polyglycolic acids, polymeric amino acids and amino acid copolymers.

The composition according to the invention may as well be provided by arranging the two active components, namely the neuraminidase inhibitor and the peptide, as described above, in a spatially separated form, that is in form of a set, which is comprised of at least a neuraminidase inhibitor and a peptide (each provided in a separate container). Accordingly, the present invention relates to a set as well, which is comprised of at least a neuraminidase inhibitor and a peptide (each provided in a separate container). The separate administration (spatially, but also temporarily) of the peptide and the inhibitor, which is made possible by this, is mainly preferred in those cases in which different administration routes of the two active components according to the invention are desired for a respective patient. For example, Oseltamivir is given orally in most cases, whereas the peptide to be used according to the invention is mainly given inhalatively. In many cases, however, a simultanous administration is desired; Zanamivir, for example, is administered inhalatively as well. Of course it may be indicated to provide an oral inhibitor systemically by way of inhalation. In some cases, the peptide to be used according to the invention can be mixed with the neuraminidase inhibitor only with difficulty, for example if the inhibitor is administered i.v. or orally and the peptide inhalatively. In many cases, however, the inhibitor and the peptide can be administered inhalatively in admixture, whereby the inhibitor directly reaches into the lung and possibly through the lung into the blood (influenza viruses are present in the lung tissue first).

In such a set according to the invention, comprising the neuraminidase and peptide components separately, the features described herein and the preferred embodiments for the mixed composition can of course be provided in all kinds of combinations perceivable to a person skilled in the art.

The drug according to the invention may for example be administered by giving the peptide of the present invention in a dosage of between 1 μg/kg and 10 mg/kg, more preferred between 10 μg/kg and 5 mg/kg, and most preferred between 0.1 and 2 mg/kg. Preferably, it is given as a bolus dose. A continuous inhalation or infusion or a repetitive dosing regime may be employed as well.

Particularly preferred compositions according to the invention contain, independently of each other,

- the peptide in an amount of 1 μg to 10 g, preferably of 10 μg to 1 g, in particular of 1 mg to 100 mg, and
- the inhibitor of viral neuraminidase in an amount of 1 μg to 10 g, preferably of 100 μg to 1 g, in particular of 1 mg to 200 mg.

Particularly preferred compositions according to the invention in a liquid form contain, independently of each other,

- the peptide in an amount of 1 μg to 10 g, preferably of 10 μg bis 1 g, in particular of 1 mg to 100 mg, and
- the inhibitor of viral neuraminidase in an amount of 1 μg to 10 g, preferably of 100 μg to 1 g, in particular of 1 mg to 200 mg, and are provided in a volume of 0.5 to 10 ml, in particular in a volume of 1 to 5 ml.

The composition according to the invention can preferably be administered in a dry form via a powder inhaler. Examples of such powder inhalers, which may be employed in the present invention, are described in U.S. Pat. Nos. 4,995,385 and 4,069,819; already established products are SPINHALER®, ROTAHALER®, FLOWCAPS®, INHALATOR®, DISKHALER® and AEROLIZER®.

The composition according to the invention can preferably be administered as an aerosol by means of a fluid nebulizer as well. Examples of such fluid nebulizers are established products such as Aeroneb® and Pari®.

According to a preferred embodiment, the composition according to the invention is characterized by a peptide and/or an inhibitor of viral neuraminidase being provided in a nebulizable powder formulation or in a nebulizable fluid formulation.

The composition according to the invention is preferably used for the treatment and prophylaxis of infections with the influenza virus type A and type B, in particular type A. In principle, however, the composition is suitable to prevent or treat an infectious disease by any possible strain of the influenza virus, which may cause this disease in an animal or in a human being. The databases relevant for information about the various influenza types are well-known to persons skilled in this art; in particular, many isolated strains of type A are described or even sequenced.

The invention will be explained in more detail by way of the following examples and drawings, to which it is not limited, of course.

It is shown in

FIG. 1: the relative lung weight of C57BL/6 mice on days 3, 5, 7 and 9 following an infection with influenza A or (as a control) without infection;

FIG. 2: the relative lung weight of C57BL/6 mice on days 5, 7 and 9 following an infection with influenza A and treatment with Oseltamivir, treatment with the composition according to the invention, and without treatment (with PBS, for a control);

FIG. 3: the relative lung weight of C57BL/6 mice on days 7 and 9 following an infection with influenza A and treatment with Zanamivir, treatment with the composition according to the invention, and without treatment (with PBS, for a control).

EXAMPLES

The present examples are provided to show in an approved experimental mouse model that the goal of the present invention has been achieved by administering to mice, which had been infected with influenza virus, a neuraminidase inhibitor or a combination of the neuraminidase inhibitor and the synthetic peptide AP301 (SEQ ID NO: 1).

Example 1

Infection with influenza virus causes the development of a pulmonary inflammation.

Laboratory mice (strain C57BL/6, 8 weeks old) were infected per-nasal with the influenza strain A (PR8/34) at a dose of 150 PFU. On days 3, 5, 7 and 9 following the infection, the lungs were taken out of 8 mice, respectively, and the relative lung weight was determined as a measure of the pulmonary inflammation.

The examination showed that with increasing length of time following the mice's infection with the influenza virus the lung weight strongly increased compared to control lungs. The results are shown graphically in FIG. 1.

Example 2

Treatment of the pulmonary inflammation by administering the neuraminidase inhibitor or administering a combination of neuraminidase inhibitor and peptide AP301.

Laboratory mice (strain C57BL/6, 8 weeks old) were infected per-nasal with the influenza strain A (PR8/34) at a dose of 150 PFU. Subsequently, each test animal received an oral administration of 10 mg/kg Oseltamivir (neuraminidase inhibitor) and an intratracheal administration of 10 μg/test animal of peptide AP301. The treatment was repeated on test days 2 and 4.

On days 5, 7 and 9 following the infection, the lungs were taken out of 30 mice, respectively, and the relative lung weight was determined as a measure of the pulmonary inflammation. The results are shown graphically in FIG. 2.

The examination showed that the neuraminidase inhibitor exhibited just a moderate effect on reducing the pulmonary inflammation, as measured by the lung weight. If, however, peptide AP301 was administered to the mice infected by the influenza virus in addition to the neuraminidase inhibitor, the pulmonary inflammation was essentially more reduced.

Example 3

Ex vivo assessment of proinflammatory properties of the AP301 peptide in human whole blood.

An ex vivo safety pharmacological study concerning the AP301 peptide in human whole blood was performed to assess whether the AP301 peptide results in the release of the proinflammatory marker interleukin-6 (IL-6) from fresh human whole blood (i.e. whether APN 301 exhibits TNF-specific inflammatory activity (i.e. TNF receptor binding activity)). In this study, fresh human whole blood has been used, as it represents an approved predictive model system for the assessment of inflammatory response in vivo.

Summary of Methodology

It was the goal of this study to determine the proinflammatory signalling capacity of the peptide AP301. Whole blood cultures were used and the secretion of interleukin-6 (IL-6), a very sensitive marker for proinflammatory stimulation, was quantified by ELISA.

Test System

| Test system | 25 ml of freshly taken heparinized blood from 5 healthy volunteers (HV) was used in the tests. |
|---|---|
| Test item | |
| Identification: | AP301 peptide (dose: 1 ng/ml to 10 µg/ml; single administration in solution) |
| Description: | White powder, purity 96% |

Whole Blood Cultures

Whole blood (WB) cultures are performed by pipetting 1 ml WB into wells of 24-well-plates. In each experiment, unstimulated and control-stimulated cultures were included.

If possible, the substances and stimulants to be investigated were always added in an identical volume to each well of a given experiment, which is not greater than 10% of the total volume contained in a well. Unstimulated controls received PBS. Volume adjustments and dilutions for different treatments were also done with PBS.

The content of each well was mixed and the plates incubated at 37° C. and 5% $CO_2$ for 24 hours. After incubation the content of each well was transferred to a fresh 1.5 ml microtube and centrifuged at 8,000-9,000×g for 15 minutes. The supernatant of each sample was transferred individually to two 1.5 ml microtubes and kept at −20° C. until use.

Detection of Interleukin-6

Interleukin-6 was quantified by a specific ELISA (Human IL-6 ELISA Set, BD Biosciences, Cat. No. 555220) employing an anti-human IL-6 antibody as capture antibody, a biotinylated anti-human IL-6 detection antibody, avidin-horseradish peroxidase conjugate as enzyme reagent and recombinant IL-6 as standard. Absorbance measurement was performed at 450 nm using the Packard FusionReader.

Data Analysis

The results for each plate were stored and evaluated using the FusionDataAnalysis Software.

Summary of Study Results

It was the goal of this study to determine the proinflammatory signalling capacity of the AP301 peptide. Whole blood cultures were used and the secretion of IL-6, a very sensitive marker for proinflammatory stimulation, was quantified by ELISA.

Whole blood samples of five healthy volunteers were either left unstimulated (negative control), stimulated with high and low doses of LPS (positive controls), or incubated with peptide with nine semi-logarithmic dilutions ranging from 10 µg/ml to 1 ng/ml. The results are shown in the following table:

TABLE

Release of interleukin-6 from fresh human whole blood on addition of peptide AP301 and LPS

| Concentration | AP301 peptide | Positive control (LPS) concentration of IL-6 (pg/ml, n = 5) |
|---|---|---|
| 0 (negative control) | less than 0.5 | less than 0.5 |
| 10 mg/ml | less than 0.5 | 195.640 |
| 1 mg/ml | less than 0.5 | 108.370 |
| 3 ng/ml | less than 0.5 | 34.867 |
| 1 ng/ml | less than 0.5 | not determined |

The results clearly reveal that the AP301 peptide did not induce any detectable level of IL-6 secretion at any of the concentrations tested. The positive controls (LPS) resulted in a strong induction of IL-6 secretion.

Discussion

The experiments have been performed to assess whether the AP301 peptide mediates the induction of a proinflammatory cascade. Readout parameter was the induced secretion of IL-6 in whole blood cultures from five healthy donors. The results clear showed that the AP301 peptide did not induce any detectable level of IL-6 in any donor's cultures. Therefore, it is demonstrated that the AP301 peptide did not induce a proinflammatory response in the chosen ex vivo model and, thus, does not exhibit any TNF receptor binding activity.

Example 4

Treatment of pulmonary inflammation by administering neuraminidase inhibitor (Zanamivir) or administering a combination of neuraminidase inhibitor (Zanamivir) and peptide AP301.

Laboratory mice (strain C57BL/6, 8 weeks old) were infected per-nasal with the influenza strain A (PR8/34) at a dose of 150 PFU. Subsequently, each test animal received a nasal administration of 1.5 mg/kg Zanamivir (neuraminidase inhibitor) and an intratracheal administration of 50 µg/test animal of peptide AP301. The treatment was repeated on test days 2 and 4.

Figure 3:
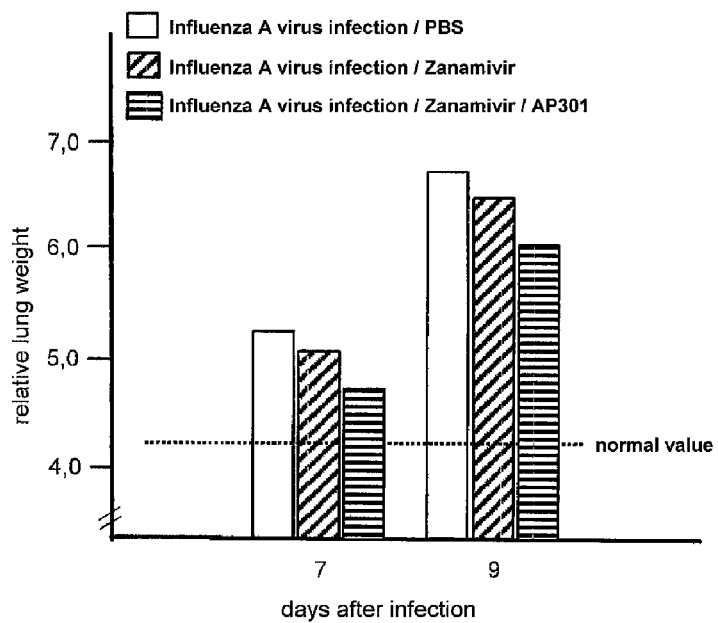

On days 7 and 9 following the infection, the lungs were taken out of 20 mice, respectively, and the relative lung weight was determined as a measure of the pulmonary inflammation. The results are shown graphically in FIG. 3.

The examination showed that the neuraminidase inhibitor (Zanamivir) exhibited just a moderate effect on reducing the pulmonary inflammation, as measured by the lung weight. If, however, peptide AP301 was administered to the mice infected by the influenza virus in addition to the neuraminidase inhibitor, the pulmonary inflammation was essentially more reduced.

Summary

The peptides according to the invention exhibit a synergistic effect in the treatment of influenza infections in combination with a neuraminidase inhibitor.

In WO 2010/099556 A1, the treatment of various pulmonary symptoms is documented, as mentioned, which is targeted to the hyperpermeability of epithelial cells and endothelial cells in such lung diseases. According to WO 2010/099556 A1 it was shown that the claimed peptides are excellently suited for preventing and treating these symptoms. Although, according to WO 2010/099556 A1, hyperpermeability of epithelial cells and endothelial cells can also be treated in cases of infections with influenza viruses (in the context of a pneumonia developing with this infection), the present invention is of course not suggested by this. The possibility of generally treating an influenza with a combination preparation, comprising this peptide, is an entirely new and inventive teaching as to the applicability of the peptide for treating a—facultatively—emerging symptom of influenza.

The basic difference can also be derived from a view into the detailed experiments according to WO 2010/099556 A1: In the examples of WO 2010/099556 A1, it is experimentally demonstrated that the peptides in the lung tissue:
i) influence the content of reactive oxygen,
ii) the effect of the bacterial gram positive toxines "listeriolysine" and "pneumolysine" also influences hyperpermeability, a.o. by regulating the level of phosphorylated myosin light chain, infiltration of leucocytes, activated protein kinase C,
iii) influence the body weight after an influenza infection,
iv) influence the body temperature after an influenza infection,
v) influence the survival rate of the test animals after an influenza infection.

Throughout the whole WO 2010/099556 A1, however, there are no experimental hints as to an infection of test animals with the influenza virus leading to an alteration of the relative lung weight and as to halting and treating such a process by the administration of the peptide. Only now, by the present invention, it is shown that an infection of the lungs of test animals with the influenza virus leads to a substantial increase in the relative lung weight.

The lung constitutes one of the most important organs of all. An increase in the relative lung weight is connected to a damage of the lung function which cannot be compensated for by any other organ. It is a property of a healthy lung to contain as many air-filled spaces (alveoles) as possible. At an increase of the relative lung weight, it must strongly be assumed that the share of air-filled alveoles will decline severely which will restrict the function of the lung. Therefore, the relative lung weight constitutes an essential factor for the treatment of influenza. The results shown in the experimental part of the present application thus demonstrate impressively the synergistic effect of the combination preparation according to the present invention, based on an extremely critical and relevant parameter.

It has hitherto been known from neuraminidase inhibitors that these may suppress the proliferation of the influenza virus. Neuraminidase inhibitors do not cause a reduction of living influenza viruses. Hitherto, it could not be shown in the state of the art that influenza virus leads to an increase of the relative lung weight. Only with the present invention has it surprisingly been shown that the administration of a neuraminidase inhibitor after an influenza infection reduces the relative weight gain of the lung weight. Additionally, by the present invention could it be shown for the first time that a simultaneous treatment of test animals, which were infected with the influenza virus, with a neuraminidase inhibitor and a peptide according to WO 2010/099556 A1 in combination results in a significant and unforeseeable synergistic effect on the relative lung weight. While neuraminidase inhibitors inhibit the proliferation of influenza virus, without reducing the already living viruses, the synergistic combination of a neuraminidase inhibitor and a peptide according to the invention obviously leads to a significant improvement of the influenza treatment. None of the drugs (neuraminidase inhibitor and the peptide according to the invention) administered individually does by itself lead to the effect shown by the present invention.

Therefore, the present invention could not be rendered obvious in any way by the results disclosed in WO 2010/099556 A1.

| Summary of sequences: | |
|---|---|
| SEQ ID NO: 1 | CGQRETPEGAEAKPWYC |
| SEQ ID NO: 2 | KSPGGQRETPEGAEAKPWYE |
| SEQ ID NO: 3 | CGQREAPAGAAAKPWYC |
| SEQ ID NO: 4 | TPEGAE |
| SEQ ID NO: 5 | QRETPEGAEAKPWY |
| SEQ ID NO: 6 | PKDTPEGAELKPWY |
| SEQ ID NO: 7 | CGPKDTPEGAELKPWYC |
| SEQ ID NO: 8 | CGQKETPEGAEAKPWYC |
| SEQ ID NO: 9 | CGQRETPEGAEARPWYC |
| SEQ ID NO: 10 | CGQRETPEGAEAKPC |
| SEQ ID NO: 11 | CQRETPEGAEAKPWYC |
| SEQ ID NO: 12 | CGQRETPEGAEAKFWYC |

The invention claimed is:

1. A composition, comprising
a peptide of the sequence CGQRETPEGAEAKPWYC (SEQ ID NO: 1), wherein the peptide has no TNF receptor binding activity and is cyclized, and
an inhibitor of viral neuraminidase,
wherein the inhibitor of viral neuraminidase is an Oseltamivir or a pharmaceutically acceptable salt thereof, wherein the composition is further defined as a nebulizable powder formulation.

2. The composition according to claim 1, characterized in that the peptide is cyclized via the C-residues.

3. The composition according to claim 1, characterized in that the peptide is cyclized via a disulfide bridge between said C-residues.

4. The composition according to claim 1, further comprising Zanamivir.

5. The composition according to claim 1, characterized in that it comprises a pharmaceutically acceptable carrier and is prepared as a pharmaceutical composition acceptable for administration to humans.

6. The composition according to claim 1, characterized in that is comprises a pharmaceutically acceptable carrier, which is selected from water, sodium chloride, sodium phosphate, sodium acetale, sodium carbonate, citrate, glycine, glycylglycine, histidine, lysine, arginine, TRIS, sodium citrate, Ringer's solution, dextrose, mannite, trehalose, saccharose, sobrite, fructose, maltose, lactose or dextrane, Hanks solution, fixed oils, ethyl oleate, stabilizing agents, pharmaceutically acceptable proteins, polysaccharides, polylactic acids, polyglycolic acids, polymeric amino acids and amino acid copolymers.

7. The composition according to claim 1, characterized in that it comprises, independently of each other,
the peptide in an amount of 1 µg to 10 g, and
the inhibitor of viral neuraminidase in an amount of 1 µg to 10 g.

8. The composition according to claim 1, characterized in that it is in a liquid form and comprises, independently of each other,
the peptide in an amount of 1 µg to 10 g, and
the inhibitor of viral neuraminidase in an amount of 1 µg to 10 g,
and is provided in a volume of 0.5 to 10 ml.

9. A set, comprising:
a first container comprising a nebulizable powder formulation comprising a peptide, of the sequence CGQRETPEGAEAKPWYC (SEQ ID NO: 1), wherein the peptide has no TNF receptor binding activity and is cyclized, and
a second container comprising an inhibitor of viral neuraminidase,
wherein the inhibitor of viral neuraminidase is an Oseltamivir or a pharmaceutically acceptable salt thereof.

10. A method of treating one or more symptom of influenza comprising the steps of:
providing a peptide of the sequence CGQRETPEGAEAKPWYC (SEQ ID NO: 1) in a nebulizable powder formulation, wherein the peptide has no TNF receptor binding activity and is cyclized, and an inhibitor of viral neuraminidase; and
treating one or more symptoms of influenza, wherein the inhibitor of viral neuraminidase treats one or more symptoms of influenza and the peptide treats pulmonary inflammation associated with influenza,
wherein the inhibitor of viral neuraminidase is an Oseltamivir or a pharmaceutically acceptable salt thereof.

11. A set for treating one or more symptoms of influenza, comprising:
a first container comprising a nebulizable powder formulation comprising a peptide of the sequence CGQRETPEGAEAKPWYC (SEQ ID NO: 1), wherein the peptide has no TNF receptor binding activity and is cyclized, and
a second container comprising an inhibitor of viral neuraminidase, wherein the first container treats pulmonary inflammation associated with influenza and the second container treats one or more symptoms of influenza,
wherein the inhibitor of viral neuraminidase is an Oseltamivir or a pharmaceutically acceptable salt thereof.

12. The composition of claim 7, wherein the peptide amount is 10 µg to 1 g, and the amount of inhibitor of viral neuraminidase is 100 µg to 1 g.

13. The composition of claim 7, wherein the peptide amount is 1 mg to 100 mg, and the amount of inhibitor of viral neuraminidase is 1 mg to 200 mg.

14. The composition of claim 8, wherein the peptide amount is 10 µg to 1 g, and the amount of inhibitor of viral neuraminidase is 100 µg to 1 g.

15. The composition of claim 8, wherein the peptide amount is 1 mg to 100 mg, and the amount of inhibitor of viral neuraminidase is 1 mg to 200 mg.

* * * * *

SEQUENCE LISTING

```
<160> NUMBER OF SEQ IDS NOS: 12

<210> SEQ ID NO 1
<211> LENGTH: 17
<212> TYPE: PRT
<213> ORGANISM: Artificial Sequence
<220> FEATURE:
<223> OTHER INFORMATION: synthetic peptide

<400> SEQUENCE: 1

Cys Gly Gln Arg Glu Thr Pro Glu Gly Ala Glu Ala Lys Pro Trp Tyr
1               5                   10                  15

Cys

<210> SEQ ID NO 2
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 2

Lys Ser Pro Gly Gly Gln Arg Glu Thr Pro Glu Gly Ala Glu Ala Lys
1               5                   10                  15

Pro Trp Tyr Glu
            20

<210> SEQ ID NO 3
<211> LENGTH: 17
<212> TYPE: PRT
<213> ORGANISM: Artificial Sequence
<220> FEATURE:
<223> OTHER INFORMATION: synthetic peptide

<400> SEQUENCE: 3

Cys Gly Gln Arg Glu Ala Pro Ala Gly Ala Ala Ala Lys Pro Trp Tyr
1               5                   10                  15

Cys

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Thr Pro Glu Gly Ala Glu
1               5

<210> SEQ ID NO 5
<211> LENGTH: 14
<212> TYPE: PRT
<213> ORGANISM: Artificial Sequence
<220> FEATURE:
<223> OTHER INFORMATION: synthetic peptide

<400> SEQUENCE: 5

Gln Arg Glu Thr Pro Glu Gly Ala Glu Ala Lys Pro Trp Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide

<400> SEQUENCE: 6

Pro Lys Asp Thr Pro Glu Gly Ala Glu Leu Lys Pro Trp Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Cys Gly Pro Lys Asp Thr Pro Glu Gly Ala Glu Leu Lys Pro Trp Tyr
1               5                   10                  15
```

Cys

<210> SEQ ID NO 8
<211> LENGTH: 17
<212> TYPE: PRT
<213> ORGANISM: Artificial Sequence
<220> FEATURE:
<223> OTHER INFORMATION: synthetic peptide

<400> SEQUENCE: 8

Cys Gly Gln Lys Glu Thr Pro Glu Gly Ala Glu Ala Lys Pro Trp Tyr
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: synthetic peptide

<400> SEQUENCE: 9

Cys Gly Gln Arg Glu Thr Pro Glu Gly Ala Glu Ala Arg Pro Trp Tyr
1               5                   10                  15

Cys

<210> SEQ ID NO 10
<211> LENGTH: 15
<212> TYPE: PRT
<213> ORGANISM: Artificial Sequence
<220> FEATURE:
<223> OTHER INFORMATION: synthetic peptide

<400> SEQUENCE: 10

Cys Gly Gln Arg Glu Thr Pro Glu Gly Ala Glu Ala Lys Pro Cys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetic peptide

<400> SEQUENCE: 11

Cys Gln Arg Glu Thr Pro Glu Gly Ala Glu Ala Lys Pro Trp Tyr Cys
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: synthetic peptide

<400> SEQUENCE: 12

Cys Gly Gln Arg Glu Thr Pro Glu Gly Ala Glu Ala Lys Phe Trp Tyr
1               5                   10                  15

Cys